(12) United States Patent
Shivaswamy et al.

(10) Patent No.: US 6,941,669 B2
(45) Date of Patent: Sep. 13, 2005

(54) METHOD FOR DETERMINING EFFECTIVE COEFFICIENT OF THERMAL EXPANSION

(75) Inventors: Satish Shivaswamy, Mason, OH (US); Richard Curless, Shelby Township, MI (US)

(73) Assignee: Magus GmbH (CH)

( * ) Notice: Subject to any disclaimer, the term of this patent is extended or adjusted under 35 U.S.C. 154(b) by 0 days.

(21) Appl. No.: 10/311,574

(22) PCT Filed: Jun. 29, 2001

(86) PCT No.: PCT/US01/20833
§ 371 (c)(1),
(2), (4) Date: Nov. 3, 2003

(87) PCT Pub. No.: WO02/03025
PCT Pub. Date: Jan. 10, 2002

(65) Prior Publication Data
US 2004/0066831 A1 Apr. 8, 2004

Related U.S. Application Data

(60) Provisional application No. 60/215,473, filed on Jun. 30, 2000.

(51) Int. Cl.⁷ .............................. G01B 5/00; G01N 25/16
(52) U.S. Cl. .............................. 33/502; 33/702; 374/55; 374/43
(58) Field of Search .............................. 374/1, 55, 43, 374/45; 33/503, 702, 502

(56) References Cited

U.S. PATENT DOCUMENTS

| | | | | |
|---|---|---|---|---|
| 4,100,837 A | * | 7/1978 | Kohler | 33/702 |
| 4,549,354 A | * | 10/1985 | Affa et al. | 33/702 |
| 4,728,232 A | * | 3/1988 | Babel | 33/702 |
| 4,776,098 A | * | 10/1988 | Nelle | 33/702 |
| 4,815,213 A | * | 3/1989 | McCabe et al. | 33/702 |
| 5,007,006 A | * | 4/1991 | Taylor et al. | 702/97 |

(Continued)

FOREIGN PATENT DOCUMENTS

GB 2227563 A * 8/1990 ............ G01B/5/03

Primary Examiner—Gail Verbitsky
Assistant Examiner—Mirellys Jagan
(74) Attorney, Agent, or Firm—Reising, Ethington, Barnes, Kisselle, P.C.

(57) ABSTRACT

A method for determining an "effective" thermal coefficient of a machine comprises the steps of installing one or more temperature sensors (110) at various locations on the machine, positioning a first machine member (60) at a "known" reference location, relative to a second machine member (42), installing a linear position measuring device (120) to detect changes in position of the first machine member (60) relative to the second machine member (42) along a first axis of movement, periodically acquiring readings from each of the temperature sensors (110) and from the linear position measuring device (120) during a test cycle and compiling the temperature and linear position data into a table. A statistical correlation analysis is performed to determine which of the temperature sensors (110) experiencing changes in temperature are most linearly related to changes in the linear position of the first machine member (60) relative to the second machine member (42) and an "effective" coefficient of thermal expansion is thereafter determined as the rate of change of position, i.e. length, relative to change in temperature. The present method includes using the machine's "effective" thermal coefficient the calibrate the motion of the machine to compensate for the thermal characteristics thereof.

15 Claims, 5 Drawing Sheets

U.S. PATENT DOCUMENTS

| | | | |
|---|---|---|---|
| 5,009,512 A | * | 4/1991 | Lessi et al. .................... 374/6 |
| 5,031,331 A | * | 7/1991 | Herzog et al. ................ 33/503 |
| 5,065,526 A | * | 11/1991 | Breyer ......................... 33/702 |
| 5,189,807 A | * | 3/1993 | Gustafsson .................. 33/702 |
| 5,333,386 A | * | 8/1994 | Breyer et al. ................ 33/503 |
| 5,446,971 A | * | 9/1995 | Neumann .................... 33/702 |
| 5,581,467 A | * | 12/1996 | Yasuda ....................... 700/193 |
| 5,650,852 A | * | 7/1997 | Chastain et al. ............... 33/702 |
| 6,167,634 B1 | * | 1/2001 | Pahk et al. .................... 33/702 |
| 6,269,284 B1 | * | 7/2001 | Lau et al. .................... 700/193 |
| 2002/0178601 A1 | * | 12/2002 | Braasch et al. ............... 33/702 |
| 2002/0189120 A1 | * | 12/2002 | Kaneda et al. ................ 33/636 |
| 2004/0028114 A1 | * | 2/2004 | Braasch et al. ............. 374/100 |

\* cited by examiner

METHOD FOR DETERMINING EFFECTIVE COEFFICIENT OF THERMAL EXPANSION

This application claims the benefit of Provisional Application No. 60/215,473, filed Jan 30, 2000.

BACKGROUND OF THE INVENTION

The present invention relates to methods for determining linear positioning inaccuracies of a moving member of a machine due to thermal expansion of the machine member and of the machine. More particularly, the present invention relates to a method for determining linear positioning inaccuracies of a moving member of a machine due to thermal expansion of the machine member and of the machine, wherein an effective coefficient of thermal expansion of the machine is derived empirically, and wherein such effective coefficient of thermal expansion is used to compensate for such positioning inaccuracies.

Large metal-working machines, such as, for example, gantry-style machine tools (oftentimes referred-to by those skilled in the art as "profiler machines"), are constructed largely out of structural steel. Like other materials used to construct machine members, steel possesses a metallurgical property which causes a machine member constructed therefrom to deform linearly in response to changes in its temperature. For example, a machine member of a long-travel machine tool—such as an elongate rail upon which another machine member rides—constructed out of steel and having a fixed length L, will change linearly in length due to changes in the temperature thereof an amount equal to:

$$\Delta L = L \cdot \alpha \cdot \Delta T \qquad (1)$$

where:

$\Delta L$ = a change in length of the member;

L = an initial length of the member at an initial temperature $T_i$ thereof;

$\alpha$ = the coefficient of thermal expansion ("thermal coefficient"); and, $\Delta T$ = a change in temperature of the member = $T_f - T_i$, where:

$T_f$ = a temperature of the member.

The thermal coefficient $\alpha$ is the rate at which a change in the length of the machine member $\Delta L$ will be directly proportional to a change in the temperature $\Delta T$ thereof and is a property of the specific material used to construct the member. Accordingly, the thermal coefficient $\alpha$ is used to calculate both increases in the length of a machine member due to increases in the temperature thereof, as well as decreases in the length of the machine member due to decreases in the temperature thereof. However, for the purpose of clarity and illustration, the within description will refer only to increases in the length of the machine member due to increases in the temperature thereof, although such description shall apply equally to decreases in the length of the machine member due to decreases in the temperature thereof without departing from either the spirit or the scope of the present invention.

The value of the thermal coefficient $\alpha$ for most materials is considered by those skilled in the art to be constant through a wide range of temperatures, including standard "room" temperature of 68° F. (20° C.), which is accepted by those skilled in the art as being a suitable (albeit generalized) baseline temperature for most thermal expansion calculations. As such, thermal expansion measurements and calculations typically are performed with reference to the initial temperature $T_i$ of the machine member being 68° F. (20° C.).

For convenience, "textbook" values of common thermal coefficients $\alpha$ which are based on an initial temperature of 68° F. (20° C.) are used typically in performing these calculations.

However, the "true" value of the thermal coefficient may be different from the "textbook" value thereof and thermal expansion measurements and calculations of machine members based on a "textbook" value of the thermal coefficient $\alpha$ may lead to inaccurate calculations, albeit generally of small magnitudes. Nevertheless, in machining operations, such as those typically performed by profiler machines, where high degrees of machining accuracy are required, even minimally inaccurate calculations may lead to significant dimensional machining errors. It is therefore desirable to provide a method for determining the "effective" value of the thermal coefficient $\alpha$ of a machine member. It is also desirable to provide a method for determining the "effective" value of the thermal coefficient $\alpha$ of a machine member, with reference to the environmental conditions surrounding it.

Machines typically are not comprised only of a single element, but rather, include combinations of numerous elements, parts, components or members which are fixedly, slidably, rotatably or otherwise operatively connected to one another to form an interrelated, operative structure For example, a profiler machine typically comprises three main sub-structures: 1) a bed upon which a workpiece is secured; 2) a head supported over the bed for positioning a cutting tool in close proximity to the workpiece for performing machining operations thereon; and, 3) a rail system for supporting the head over the bed and for providing movement of the head with respect to the bed along an elongate axis thereof. Each of the three main sub-structures includes numerous parts operatively engaging one another for performing machining operations according to a preselected design configuration, and each such part has thermal properties according to the material from which such part is constructed. As the temperature of each member increases, for example, due to an increase in the temperature of the air surrounding the machine (thereby increasing the temperature of the part itself) the members individually experience thermal expansion at a rate equal to the thermal coefficient $\alpha$ of the material from which the members are respectively constructed. It would not be uncommon for the parts to be constructed from different materials, in which case each material typically will have a unique thermal coefficient $\alpha$, and the parts of the machine will expand at different rates leading a non-uniform expansion of the machine. It is desirable therefore to provide a method for determining an "effective" value of the thermal coefficient $\alpha$ of a machine comprised of members constructed of materials having differing individual thermal coefficients $\alpha$.

Moreover, in a conventional machine, the members thereof are constrained from moving freely because the members are operatively connected to other machine members, as well as to support structures. For example, the rail system of a conventional profiler machine comprises a pair of elongate rails along which the head traverses. The rails are fixedly anchored to the machine shop floor by several structural bolts, thereby limiting the free thermal elongation of the rails. Because machining accuracy depends directly on the accurate positioning of the head along the rails, it is necessary to be able to calculate how the rails expand in response to increases in the temperature thereof. However, because the rails are constrained, conventional thermal expansion calculations based upon "textbook" values of the thermal coefficient $\alpha$ likely will not accurately predict the expansion of the rails due to increases in the temperature thereof. Accordingly, it is desirable furthermore to provide a method for determining the "effective" value of the thermal coefficient α of a machine comprised of members which are constrained from freely moving in response to changes in the temperatures thereof.

The size and geometry of conventional machine tools, such as profiler machines, oftentimes results in localized heat pockets being created at isolated locations of the machine members, thereby giving rise to localized rates of thermal expansion which are different from the rates of thermal expansion at other locations of the machine and of the machine members. That is, the temperature of the machine varies (sometimes widely) across the entire machine, making it difficult to determine where to measure the temperature of the machine, for example, for the purpose of performing "textbook" thermal expansion calculations. Accordingly, it is desirable furthermore to provide a method for determining an "effective" temperature of the machine, which such "effective temperature" thereof may be used, for example, in performing thermal expansion calculations.

It is known that machine tools must be calibrated from time-to-time to correct for mechanical and thermal positioning errors. However, while conventional machine calibration practices may adequately compensate for mechanical positioning errors, they incorporate only "textbook" values of thermal coefficients, and as such, machine compensation tables resulting therefrom do not adequately consider the unique thermal characteristics of the machine being calibrated. Accordingly, it is desirable furthermore to provide a method for calibrating a machine wherein the true thermal characteristics of the machine are closely approximated, such as, with reference to an "effective" thermal coefficient thereof. Moreover, conventional machine calibration practices do not consider the thermal characteristics of a workpiece being machined thereby. That is, machine compensation tables resulting from conventional machine calibration practices are not adapted to be modified for machining workpieces constructed out of materials having thermal characteristics differing significantly from the thermal characteristics of the machine. For example, an aluminum workpiece will expand at a rate much greater than the rate at which a profiler machine will expand and the machine compensation tables resulting from conventional machine calibration practices reflect only the thermal characteristics of the machine, which will result in machining inaccuracies unless the NC "part program" used to instruct the machine for performing machining operations is modified to account for the unique thermal characteristics of the workpiece relative to the thermal characteristics of the machine. Oftentimes, such modification must be performed manually by an NC programmer or are incorporated into so-called "post-process" modification of the NC program. It is desirable therefore to provide a method for calibrating a machine wherein the thermal characteristics of a workpiece to be machined thereby are incorporated thereinto. It is desirable even further to provide a method for calibrating a machine wherein the thermal characteristics of a workpiece to be machined thereby are incorporated thereinto, and wherein a plurality of workpiece materials may be considered.

SUMMARY OF THE INVENTION

The present invention is for a method for determining an "effective" thermal coefficient of a machine comprised of members and for a method for using such effective thermal coefficient to calibrate the machine and of the members thereof for thermal expansion thereof. The method for determining an "effective" thermal coefficient of a machine according to the preferred embodiment hereof comprises the steps of installing one or more temperature sensors, such as conventional thermocouples, at various locations on the machine, positioning a first machine member at a known "reference" location, relative to a second machine member, installing a linear position measuring device to detect changes in position of the first machine member relative to the second machine member along a first axis of movement, periodically acquiring readings from each of the temperature sensors and from the linear position measuring device during a test cycle and compiling the temperature and linear position data into a table. The test cycle preferably is a period of time, for example, 24 hours to 48 hours, during which diurnal temperature variation of the environment surrounding the machine will occur. A statistical correlation analysis, such as by using the Pearson Product Moment Correlation Coefficient, is performed to determine which of the temperature sensors experiences changes in temperature which are most linearly related to changes in the linear position of the first machine member relative to the second machine member. An "effective" coefficient of thermal expansion is thereafter determined as the rate of change of position (or length) relative to change in temperature. The position of the temperature sensor which most linearly relates to changes in the linear position of the first machine member relative to the second machine member, then, defines the location of the "effective" temperature of the machine.

The present invention also relates to a method of using the machine's "effective" thermal coefficient to calibrate the motion of the machine to compensate for the thermal characteristics thereof. That is, compensation tables resulting from the machine calibration procedure are based at least partly on the "effective" thermal coefficient of the machine. The compensation table may be modified to take into account the thermal characteristics of a workpiece to be machined, which such workpiece may be constructed from any one of a plural of materials having differing thermal coefficients. Compensation table can be changed altogether to permit machine compensation for different workpiece materials. Compensation table selection can be manual, such as by an operator selecting an option on the machine control, or automatic, such as by a program instruction in the part program.

According to one aspect of the present invention, the present invention provides a method for calibrating a machine to compensate for thermal expansion/contraction thereof characterized in that the method comprises the steps of determining an effective thermal coefficient of the machine, and generating a machine thermal compensation value for at least one of a predetermined number of preselected position values, the machine thermal compensation value being based on the effective thermal coefficient of the machine.

It is an object of the present invention to provide a method for determining an "effective" value of the thermal coefficient of a machine member or machine.

It is another object of the present invention to provide a method for determining an "effective" value of the thermal coefficient of a machine member or machine, with reference to the environmental conditions surrounding it.

It is still another object of the present invention to provide a method for determining an "effective" value of the thermal coefficient of a machine comprised of members constructed of materials having differing individual thermal coefficients.

It is yet another object of the present invention to provide a method for determining an "effective" value of the thermal coefficient of a machine comprised of members which are constrained from freely moving in response to changes in the temperatures thereof.

It is still another object of the present invention to provide a method for determining an "effective" temperature of a machine member or machine, which such "effective temperature" thereof may be used, for example, in performing thermal expansion calculations.

It is another object of the present invention to provide a method for calibrating a machine wherein the true thermal characteristics of the machine are closely approximated, such as, with reference to an "effective" value of a thermal coefficient thereof.

It is still another object of the present invention to provide a method of calibrating a machine wherein the thermal characteristics of a workpiece to be machined thereby are incorporated thereinto.

It is another object of the present invention to provide a method for calibrating a machine where the thermal characteristics of a workpiece to be machined thereby are incorporated thereinto, and wherein a plurality of workpiece materials may be considered.

These and additional objects, features and advantages of the present invention will become apparent to those reasonably skilled in the art from the description which follows, and may be realized by means of the instrumentalities and combinations particularly pointed out therein

BRIEF DESCRIPTION OF THE DRAWINGS

A better understanding of the present invention will be had upon reference to the following description in conjunction with the accompanying drawings in which like numerals refer to like parts, and wherein.

Figure 1:
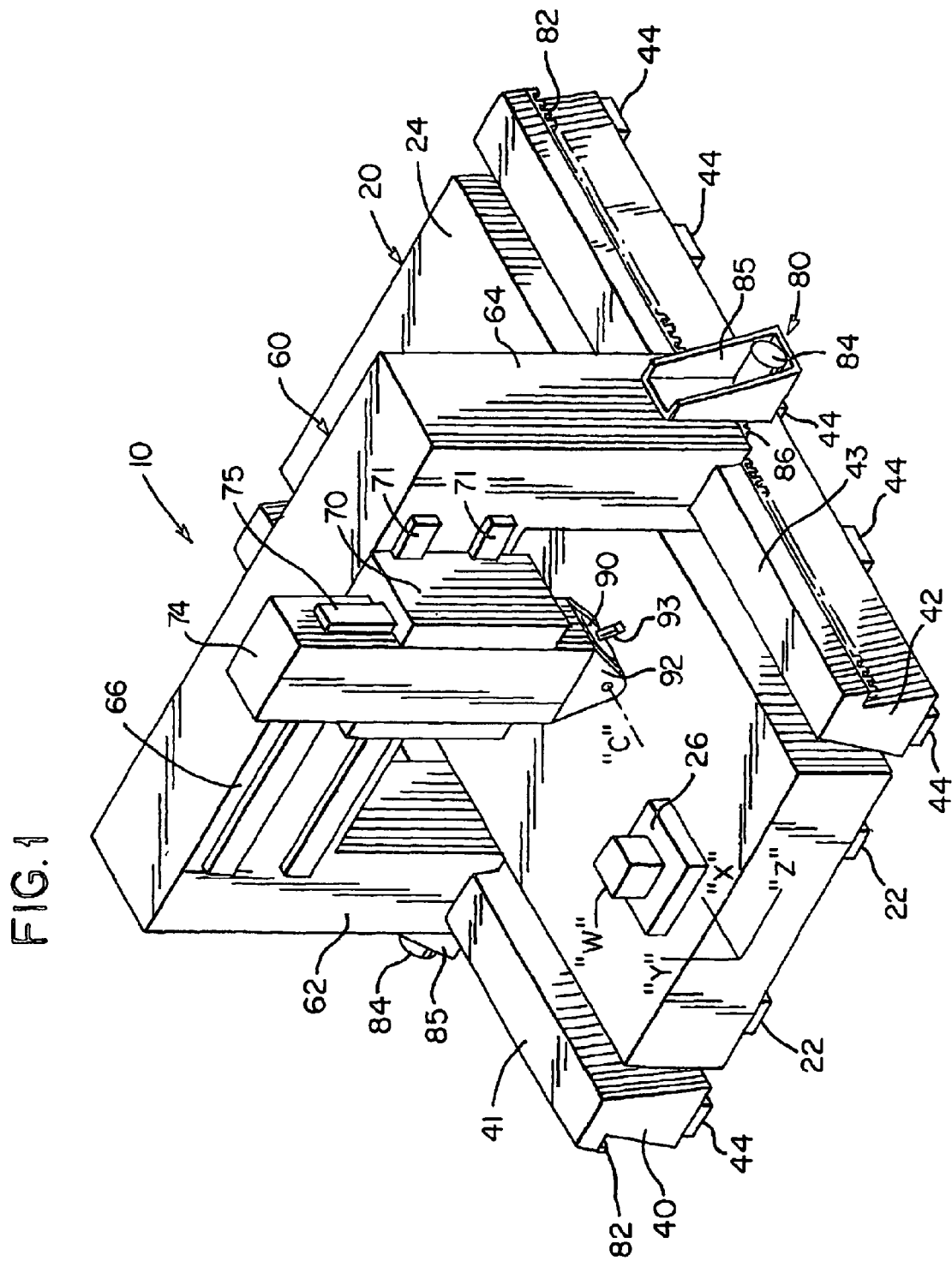
FIG. 1 is a schematic perspective view of a conventional gantry-style machine tool.

DETAILED DESCRIPTION OF THE PREFERRED EMBODIMENTS with reference to FIG. 1, a gantry-style machine tool 10 (sometimes referred-to herein as a "profiler" machine) includes an elongate bed 20 resting on pads 22 and being anchored to the machine shop floor, such as, by structural bolts (not shown), connecting the bed 20 to the floor through the pads 22. A lengthwise direction of the bed 20 defines an "X" axis thereof. The bed 20 preferably is constructed from a single piece of structural steel (as shown) having a substantially continuous planar work surface 24 which is machined to have a flat, uniform finish. Alternatively, the bed 20 may be constructed from a plurality of sections (not shown), in which case the sections are connected to one another to form the work surface 24.

A workpiece-holding device 26 is securely affixable to the work surface 24 at any number of a plurality of locations thereon and is adapted to securely hold a workpiece "W" thereto. Alternatively, the workpiece "W" may be securely affixed to the work surface 24, such as, by clamping, in which case, the workpiece-holding device 26 is not necessary.

First and second elongate rails 40, 42, respectively, resting on pads 44, are positioned alongside the bed 20, spaced transversely therefrom along a transverse direction along axis "Z", which is perpendicular to axis "X". The rails 40, 42 extend in a direction parallel to the "X" axis, and are mounted to the machine shop floor, such as, by structural bolts (not shown) such that the rails 40, 42 are parallel to one another. The rails 40, 42 preferably are constructed from structural steel and include upper bearing surfaces 41, 43 which have been machined to have a flat, uniform finish. The rails 40, 42 may be separate from the bed 20 (as shown) or may form an integral construction with the bed 20. The bearing surfaces 41, 43 may be machined directly on the rails 40, 42, respectively, or alternatively, may be in the form of elongate rail caps (not shown) which are affixed to the rails 40, 42.

A machining head 60 is supported over the bed 20 by rails 40, 42 and is movable relative thereto along the "X" axis of the bed 20. For example, the head 60 includes first and second upright supports 62, 64 having upper ends thereof connected to one another by an overhead bridge structure 66. A lower end of the first upright support 62 is slidably positioned along the first rail 40 and a lower end of the second upright support is slidably positioned along the second rail 42 such that simultaneous movement of the supports 62, along the rails 40, 42 positions the overhead bridge 66 at any of an infinite number of locations along the "((X))" axis of the bed 20.

The machining head 60 is movable along the rails 40, 42, such as, by a rack-and-pinion assembly 80, shown schematically in FIG. 1 and described herein with reference to the second rail 42. The rack-and-pinion assembly 80 includes an elongate rack 82 mounted to the rail 42, extending therealong parallel to axis "X". A reversible motor 84 or other similar drive device is mounted to the second upright support 64, such as, by bracket 85, such that a pinion 86 mounted to an output shaft (not shown) of the motor 84 positively engages the rack 84. A similar rack-and-pinion assembly 80 is provided on the first rail 40. Rotation of the pinion 86, then, such as, by energizing the motor 84, drives the machining head 60 along the rails 40, 42. Alternatively, the rack-and-pinion assembly 80 may be replaced with another linear drive device, such as a conventional ballscrew drive assembly or a conventional linear servomotor drive assembly.

The machining head 60 also includes a transverse carrier 70 slidably mounted to the overhead bridge 66 for movement of the transverse carrier 70 along horizontal ways 71 in a direction parallel to the "Z" axis. The transverse carrier 70 may be driven by any conventional linear drive device (not shown), such as a rack-and-pinion assembly, a ballscrew drive assembly, a linear servomotor assembly or the like. A spindle carrier 74 is slidably mounted to the transverse carrier 70 for movement of the spindle carrier 74 along vertical ways 75 in a direction parallel to the "Y" axis. The spindle carrier 74 may be driven by any conventional linear drive device (not shown), such as a rack-and-pinion assembly, a ballscrew drive assembly, a linear servomotor assembly or the like.

A spindle 90 is mounted to a lower end of the spindle carrier 74, such as, by bracket 92 such that the spindle 90 is adapted to pivot about a "C" axis, which is parallel to the "X" axis. The spindle 90 is adapted to hold, such as, for example, by a chucking device (not shown), a conventional cutting tool 93. Movement of the cutting tool 93, relative to the workpiece "W", then, may be along any combination of four axes; namely, the "X" axis, the "Y" axis, the "Z" axis and the "C" axis. Additional degrees of movement of the cutting tool 93, relative to the workpiece "W", may be added according to structures and techniques known to those skilled in the art. Moreover, spindle 90 may be mounted to carrier 74 without provision for movement about the "C" axis, in which case, spindle 90 would direct tool 93 in a direction, for example, parallel to axis "Y", axis "Z", or any oblique axis relative thereto. The configuration of the machine tool 10 described herein is for the purpose of illustration only and the present invention is not limited thereto, but rather, may be practiced on any machine, subassembly or component thereof, which may become obvious to one of ordinary skill in the art upon reading the within description.

Figure 2:
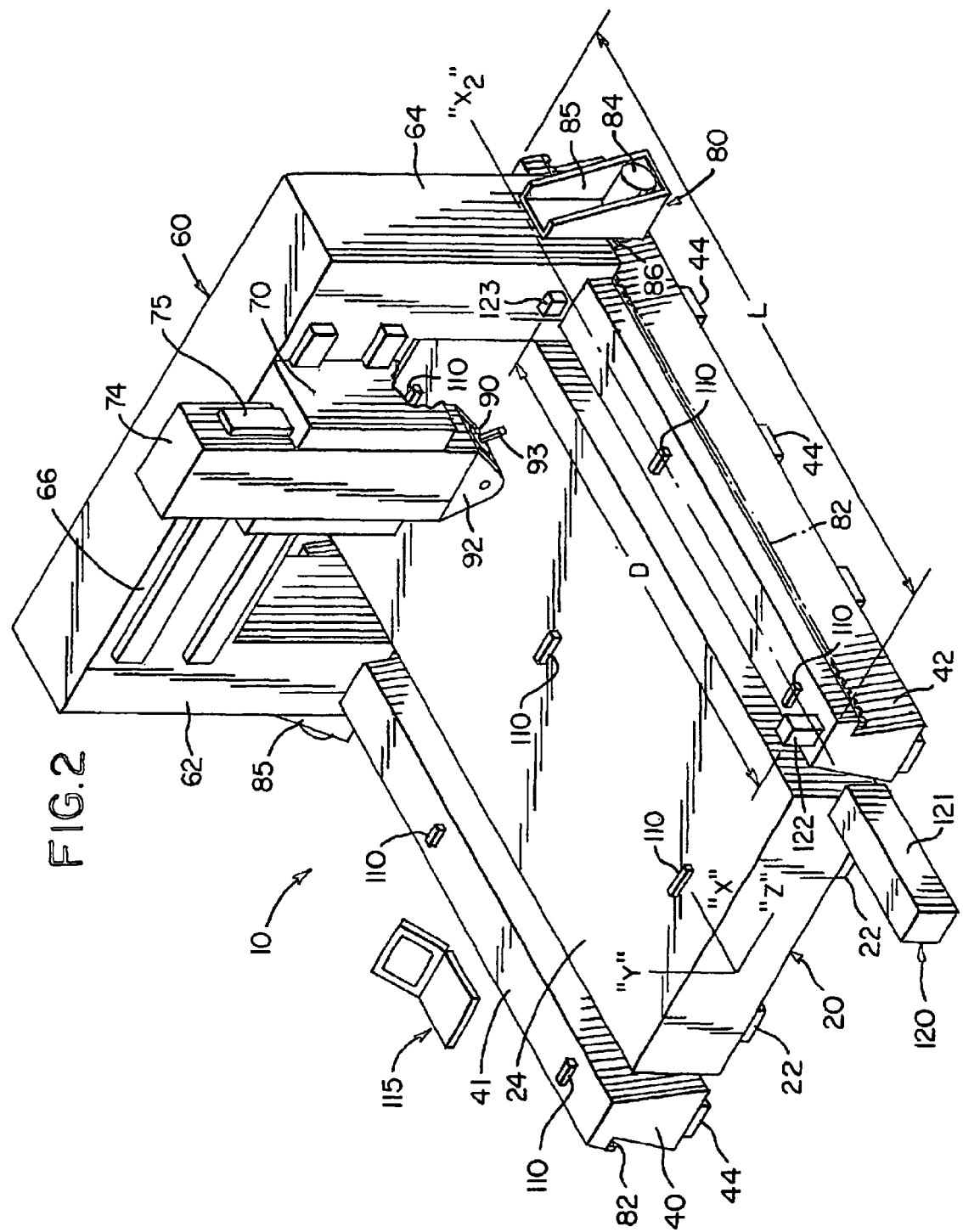
FIG. 2 is a schematic perspective view of the machine tool of FIG. 1, showing instrumentation installed thereon for use with the method according to a preferred embodiment of the present invention.

With reference to FIG. 2, the machine tool 10 is prepared for determining an "effective" coefficient of thermal expansion a ("thermal coefficient") of the machine tool 10 according to a preferred embodiment of the present invention. Although the method according to the preferred embodiment hereof will be described with reference to expansion of the second rail 42 of the machine tool 10 along the "$X_2$" axis, it will be obvious to those of ordinary skill in the art, upon reading the within detailed description, that the method according to the preferred embodiment hereof may be modified to determine the coefficient of thermal expansion a of the machine tool 10 (or of any member thereof) along any axis without departing from either the spirit or the scope hereof For example, the method of the present invention may be used to determine an "effective" coefficient of thermal expansion to calibrate movement of the transverse carrier 70 along horizontal ways 71 in the "Z" direction or to calibrate movement of the spindle carrier 74 along ways 75 in the "Y" direction.

In the exemplary embodiment hereof the "effective" thermal coefficient α will be derived empirically for the purpose of calibrating movement of the head 60 along the rails 41, 42 and will be described with reference to second rail 42. As stated above, owing to thermal expansion characteristics of the material used to construct the rail 42, the length of the rail 42 will be different at 68° F. (20° C.) room temperature than under normal operating circumstances, where the temperature is usually greater than 68° F. (20° C.) room temperature. The difference between the length L of the rail 42 at 68° F. (20° C.) room temperature and the length L of the rail 42 at normal operating conditions is quantified and represented herein as ΔL, the change in the length thereof owing to thermal expansion of the rail 42. Changes in the length of the rail 42 are desired so that the machining head 60 can be positioned along the "X" axis accurately, relative to the workpiece "W", while taking into account thermal expansion of the rail 42 along the "X" axis.

One or more temperature sensors 110, such as, for example, conventional thermocouples, are installed at various locations across the bed 20, the rails 40, 42 and the machining head 60. The quantity and positioning of the sensors 110 is determined based upon known operating conditions of the machine 10. That is, an operator who is skilled with operation of the machine 10 may know from fist-hand experience that certain locations on the machine 10 experience local "hot spots," in which case, the operator may choose to install several sensors 110 in the general region of such a "hot spot" Similarly, the operator may know from first-hand experience that certain locations on the machine 10 experience substantially uniform temperature distribution, in which case, the operator may choose to install only one sensor 110 in this location. For example, several criteria may be used to determine the quantity and positioning of the sensors 110, such as, the axis of the machine being tested, the feedback system of the machine, factory air temperature control vents, heat sources of the machine and the machine environment, generally.

In the exemplary embodiment, nine sensors 110 are used, three of which are installed equally-spaced along the first rail 40 (only two of which are shown), three of which are installed equally-spaced along the second rail 42 (only two of which are shown) and three of which are installed equally-spaced along the "X" axis of the bed 20. The sensors 110 may be installed on the surface of the machine 10, or may be embedded therein, such as by drilling a hole in the machine 10 and inserting the sensor 110 in the hole formed thereby. The sensors 110 are electronically coupled, such as by cables (not shown), to a data collection device 115, such as a laptop personal computer ("PC") having sufficient conventional hardware and software for interfacing with the sensors 110 and for reading and recording temperatures detected thereby.

A linear position measurement device 120, such as a model HP5529A laser measuring device sold by Agilent Technologies of Palo Alto, Calif., is installed at a front end of the rail 42 and aligned with a second rail axis "$X_2$", which such second rail axis "$X_2$" is parallel to the "X" axis of the bed 20, to measure the position of the head 60 relative to the rail 42 therealong. The laser measurement device 120 includes a laser transmitter/receiver 121 positioned in front of the rail 42 and aligned with the second rail axis "$X_2$" to transmit a laser light beam along the second rail axis "$X_2$" towards the head 60, an interferometer 122 mounted near the front of the rail 42 and a linear retroreflector 123 mounted to the second upright support 64 of the head 60. The interferometer 122 and the retroreflector 123 are aligned with the transmitter/receiver 121 along the second rail axis "$X_2$". The transmitter/receiver 121 is electronically coupled to the PC 115, which is adapted to receive data from the transmitter/receiver 121 and to store the data, along with temperature data acquired from the sensors 110. The laser measuring device 120 is calibrated to accurately measure, using conventional techniques, a distance "D" between the interferometer 122 and the retroreflector 123, which of course, is a function of both time and temperature. The linear measurement device 120 is calibrated according to the manufacturer's instructions, and where auxiliary sensors have been provided with the device 120 to obtain environmental conditions data, for example, air temperature, pressure and humidity—all of which may affect the accuracy of the linear measurement device 120—such sensors are installed and enabled such that the device 120 is prepared to obtain highly accurate measurements. If the control system of the device 120 requires a value of the thermal coefficient α of the machine 10, a value of zero should be entered such that no analytical correction of the linear measurements obtained by the device 120 owing to thermal expansion thereof is made, but rather, such that the device 120 obtains (and records) the true value of any linear measurements detected thereby. It will be readily understood by those skilled in the art that the laser measurement device of the exemplary embodiment, and the components thereof, are described herein for the purpose of illustration only and the present invention is not limited to this type of linear measurement device, but rather, any device which is suitable for accurately measuring small changes in distance, for example, on the order of ±0.00001 inches (0.25 microns), may be substituted for the laser measurement device without departing from either the spirit or the scope hereof.

The PC 115 includes software which is adapted to receive measurements from the sensors 110 and from the linear position measurement device 120 and to tabulate the data acquired thereby. The software is adapted to periodically acquire data from the sensors 110 and from the linear position measurement device 120, for example, every 10 minutes, for a predetermined extended period of time, for example, 24 hours, which such extended period of time has been selected to account for diurnal variations in the temperature of the machine 10. Of course, temperature and position measurements may be obtained at any predetermined interval (for example, more or less than 10 minutes) and for any predetermined test period (for example, more or less than 24 hours).

The method of determining the "effective" thermal coefficient α according to the preferred embodiment hereof will now be described. After the machine tool 10 has been prepared as described above and shown in FIG. 2, the head 60 is moved to the near end (adjacent the interferometer 123) of the rails 40, 42 and the linear measurement device 120 is "zeroed", thereby defining a "home" position of the head 60, relative to the rails 42. The head 60 is then moved to the far end of the rails 40, 42 (as shown) and "parked" in this position. The distance traveled by the head 60 from the "home" position to the "parked" position, as measured by the measurement device 120, is recorded by the PC 115 and is identified as the test length "$L_T$". The measurement device 120 is again "zeroed", thereby defining a "reference test position".

The test procedure software, which has been installed on the PC 115 is initiated and will run for the predetermined test period, which in the preferred embodiment hereof is 24 hours. At some predetermined frequency, which in the preferred embodiment hereof has a period of 10 minutes, the test procedure software acquires a temperature reading from each of the sensors 110 and a position reading from the linear measurement device 120 and stores these readings in a table in the memory (or some other suitable storage media) of the PC 115. The position reading acquired from the linear measurement device 120 at the end of the 10-minute interval corresponds to the position of the head 60 relative to the "reference test position" and is a measure of the so-called "drift" of the head 60 from the "reference test position" due to thermal expansion/contraction of the machine 10, or more particularly, due to thermal expansion/contraction of the rail 42. Head "drift" from the "reference test position", then, will be known for each 10-minute interval of the test procedure. Using the nomenclature stated above with respect to thermal expansion calculations, the thermal "drift" is represented by the change in length ΔL of the rail 42 due to thermal expansion/contraction.

Once the test procedure is complete, a statistical correlation analysis is performed on the data acquired by the temperature sensors 110 and the linear measurement device 120 and stored in the memory (or on some other suitable storage media) of the PC 115 to determine which of the sensors 110 detects a temperature change ΔT which most directly correlates to a linear change in the length ΔL of the rail 42. Although any suitable statistical model may be used, a Pearson Product Moment Correlation Coefficient preferably is calculated for each temperature sensor 110, using the data acquired thereby, according to the following equation:

$$R = \frac{n(\Sigma XY) - (\Sigma X)(\Sigma Y)}{\sqrt{[n\Sigma X^2 - (\Sigma X)^2][n\Sigma Y^2 - (\Sigma Y)^2]}} \quad (2)$$

where:

R the Pearson Product Moment Correlation Coefficient;

n=the number of data samples acquired during the test period;

X=temperature readings obtained from the sensors 110; and,

Y=machine "drift" readings obtained from device 120.

As stated above, the values for Y correspond to the readings obtained from the linear measurement device 120 at the end of each 10-minute interval between data acquisition events. A series of "$R^2$" correlation coefficient values are thereby calculated, one such "$R^2$" value being calculated for each sensor 110, to provide a statistical measurement of the degree to which temperature changes detected by that sensor 110 directly correlates to changes in the length ΔL of the rail 42, as detected by the linear measurement device 120. By definition, the closer an "$R^2$" value is to a coefficient reference of 1.0, the more the two variables analyzed thereby directly correlate with one another. Accordingly, the "$R^2$" values are compared for all sensors 110, and the sensor 110 having an "$R^2$" value closest to 1.0 is determined to be the sensor 110 most representative of the location of the "effective" temperature of the machine 10. Temperature measurements of the machine 10, then, for example, to perform thermal expansion/contraction measurements, should be taken from the sensor 110 having an "value closest to 1.0. Where none of the "$R^2$" values of the sensors 110 are close to 1.0, such as, for example, all sensor "$R^2$" values being less than 0.5, it should be determined that none of the sensors 110 are located in a position on the machine 10 which sufficiently represents the "effective" temperature of the machine 10, and the sensors 110 should be repositioned and the test procedure repeated until an "$R^2$" value sufficiently close to 1.0 is obtained.

Figure 3:
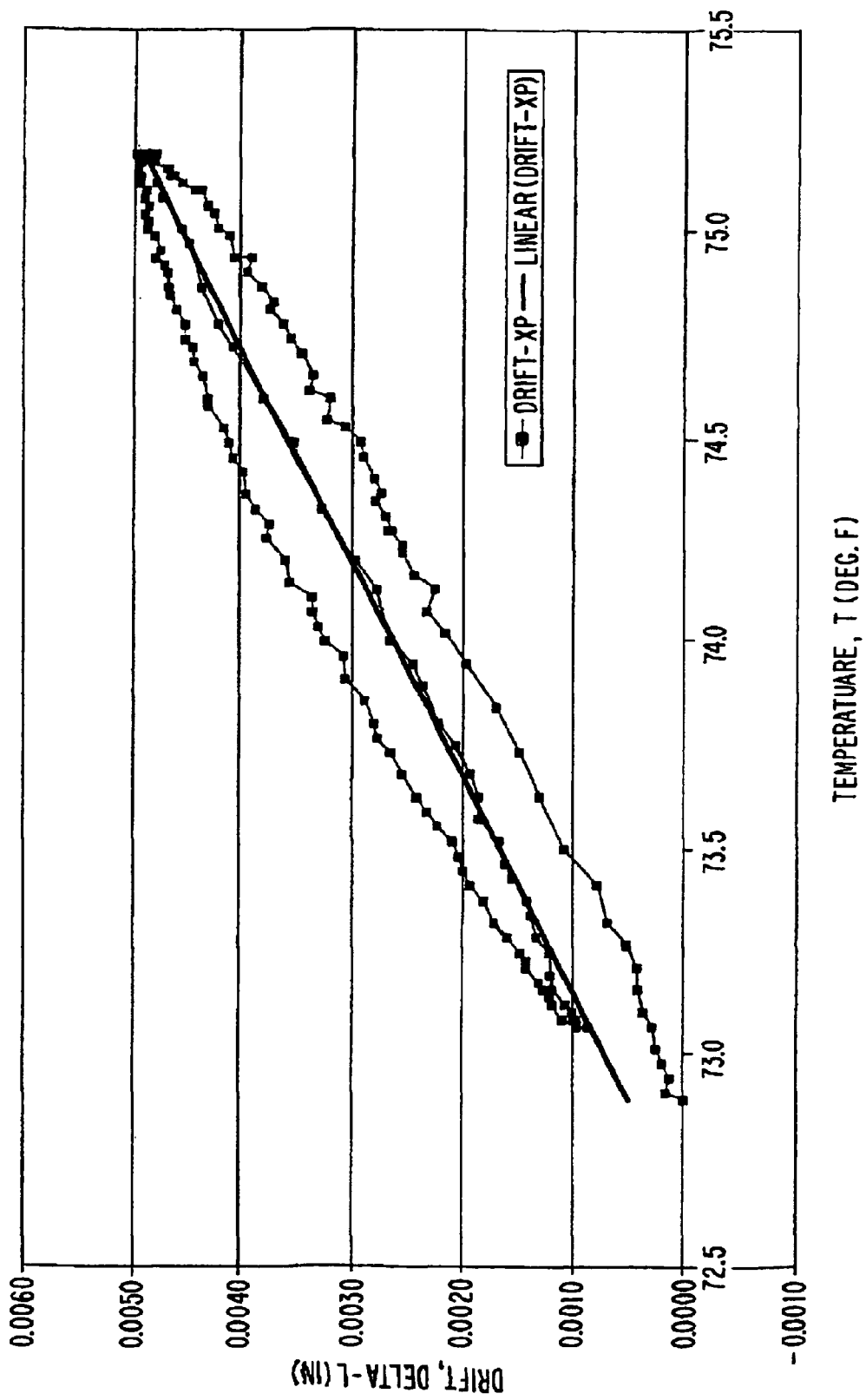
FIG. 3 is a plot of machine "drift" versus temperature used to determine an "effective" coefficient of the thermal expansion of the machine tool of FIG. 1 according to a preferred embodiment of the present invention.

To determine the "effective" thermal coefficient α of the machine 10, and more particularly for the purpose of illustration, of the second rail 42 of the machine 10, along axis "$X_2$", the temperature data acquired from the sensor 110 having an "$R^2$" value closest to 1.0 is plotted against the "drift" measurements acquired from the linear measurement device 120. With reference to FIG. 3, a linear plot is prepared of temperature changes ΔT vs. thermal "drift" ΔL and a least-squares line is fit over the plot thereof. According to Equation (1), above, the slope of the least squares line on a plot of ΔT vs. ΔL is the rate of change of ΔL with respect to ΔT. The "effective" thermal coefficient α of the machine, with respect to the "$X_2$" axis, is the slope of the least squares fit line of FIG. 3 divided by the initial length L of the machine member, which in the present invention is the test length $L_T$.

Because the thermal coefficient α is derived empirically using the above test procedure, it is referred-to herein as an "effective" thermal coefficient α, to distinguish it from the "textbook" value thereof. In many cases, the "effective"

thermal coefficient α will differ from the "textbook" value thereof and differences therebetween, say on the order of less than ±50% will typically be acceptable. However, where the determined "effective" thermal coefficient α differs greatly from the textbook" value thereof, say on the order of greater than ±50%, the test analyst must use engineering judgment to determine whether the test should be repeated, and if so, whether the sensors 110 should be repositioned.

Obtaining the effective coefficient of expansion and using that parameter for calibrating the machine initially provides the basis for future rechecks of the machine's calibration for correctness. By not using the correct coefficient initially means that when the machine is rechecked, if the temperature factors are different at the machine, the new calibration values will never match the initial setup and cause a resetting of the values. The effort for resetting is time consuming and causes loss of available production time. Even if the NC program were adjusted to allow production of a good part with an initially incorrect set of machine compensation values, the recheck of the machine will cause a resetting of compensation values and cause the machine to produce a different part. The purpose of rechecking the machine is for maintaining proper values even if the machine were to drift or change over time. One would never know if changes had occurred to the machine during maintenance check if an incorrect coefficient of expansion were used. If parts started showing errors, one would never know if the errors were due to process changes or machine changes. By using a method that obtains the effective coefficient of expansion initially for the machine installation means that a proper baseline for machine calibration is established and can be used again and again during maintenance checks.

Figure 4:
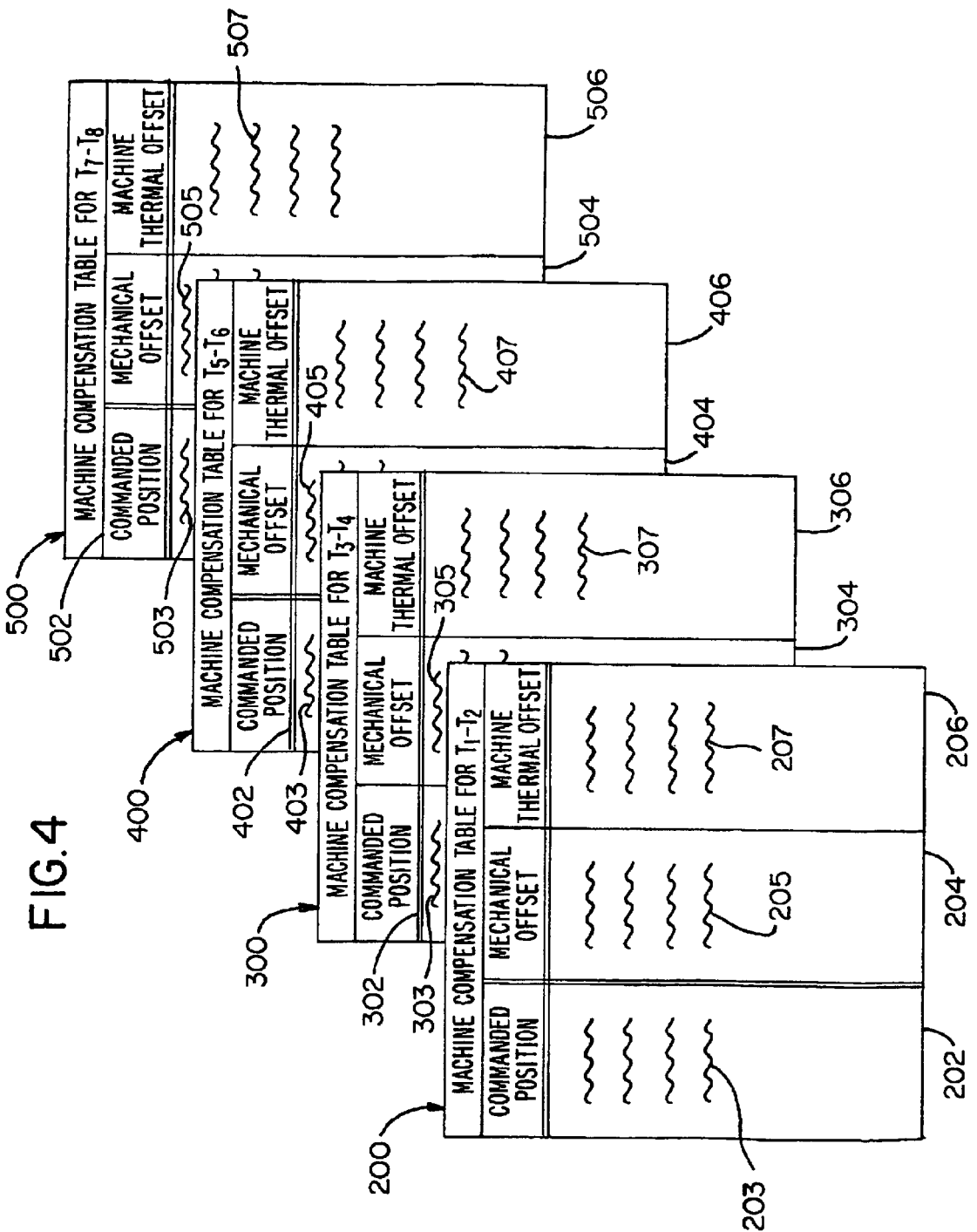
FIG. 4 is a schematic representation of a compensation table used to compensate for thermal expansion of the machine of FIG. 1 according to a preferred embodiment of the present invention; and, FIG. 5 is a schematic representation of a compensation table used to compensate for thermal expansion of the machine of FIG. 1, as well as for thermal expansion of the workpiece of FIG. 1, according to a preferred embodiment of the present invention.

With reference to FIG. 4, the value of the "effective" thermal coefficient α relative to an axis of movement may be used in calibrating movement of machine components along such axis to compensate for thermal expansion thereof A typical compensation table 200 is in the form of a look-up table residing in (or otherwise accessible to) the machine control system and includes a first column 202 of commanded position values 203 representing positions, locations or displacements which the NC program may command a machine member, for example, the head 60 of the machine tool 10 shown in FIG. 2, to move along an axis, for example, the "X" axis shown in FIG. 2. The compensation table 200 further includes a second column 204 of mechanical offset values 205, one such mechanical offset value 205 corresponding to one of each of the commanded position values 203 of the first column 202. The mechanical offset values 205 represent some offset value used to compensate for mechanical positioning errors of the machine 10, for example, due to slack in the drive mechanisms thereof and can be determined by any conventional mechanical calibration procedure.

The compensation table 200 also includes a third column 206 of machine thermal offset values 207, one such machine thermal offset value 207 corresponding to one of each of the commanded position values 203 of the first column 202. The third column 206 represents values calculated using Equation (1) to compensate for thermal positioning errors of the machine due to thermal expansion thereof. For the purpose of using Equation (1) to calculate such machine thermal offset values 207 (which are represented in Equation (1) by the term $\Delta L$) the "effective" thermal coefficient α of the machine 10 (which is determined according to the procedure described hereinabove) may be used. The term $\Delta T$ represents the difference between the operating temperature (which is represented in Equation (1) by the term $T_f$) of the machine 10 and a reference temperature ($T_i$) of 68° F. (20° C.).

Because the values 207 of the third column 206 depend directly on the operating temperature, changes in operating temperature will cause changes in the values 207. However, even though the operating temperature may vary during machining operations, such variance typically results in only modest changes to the values 207 of the third column 206. As such, it is preferable to provide a static compensation table 200 for a predetermined operating temperature range $T_1$–$T_2$, for example, between $T_1$=60° F. (15.56° C.) and $T_2$=70° F. (21.11° C.), wherein the values 207 of the third column 206 are calculated based on an average temperature within the temperature range $T_1$–$T_2$. A second compensation table 300 may be provided for a second temperature range $T_3$–$T_4$, wherein the second compensation table 300 includes first and second columns 302, 304, respectively, containing values which are identical to columns 202, 204, respectively, of compensation table 200, as well as a third column 306 of machine thermal compensation values 307 calculated using Equation (1) based upon an average temperature of the second temperature range $T_3$–$T_4$. Additional compensation tables, such as third and fourth compensation tables 400, 500, respectively, may likewise be provided for additional temperature ranges $T_5$–$T_6$ and $T_7$–$T_8$, respectively.

At the start of a machining operation, the operating temperature of the machine must be entered into the machine control such that the machine control may select the proper compensation table 200, 300, 400, 500 to be used. According to a preferred embodiment hereof, a machine operator manually inputs the operating temperature of the machine 10 into the machine control, which compares the operating temperature with the available temperature ranges $T_1$–$T_2$, $T_3$–$T_4$, $T_5$–$T_6$, $T_7$–$T_8$ and selects the proper compensation table 300, 400, 500 based thereon. Motion of the machine, then, is "compensated" for both mechanical and thermal positioning errors by adding corresponding values 205, 207 from the second and third columns 204, 206, respectively, to the corresponding commanded position value 203 from the first column 202. In this manner, modification of the NC program is not required in order to compensate for thermal expansion/contraction of the machine 10 because the machine 10 has been calibrated to compensate for such thermal characteristics.

The operating temperature of the machine 10 may be entered into the machine control by alternative means. For example, the machine control may acquire a temperature reading from a thermocouple located somewhere on the machine. As described above, the "effective" temperature of the machine 10 corresponds to the sensor 110 (FIG. 2) where the temperature readings obtained thereby during the thermal calibration procedure according to the present invention result in an "$R^2$" value closest to 1.0. Rather than requiring a machine operator to manually input the operating temperature of the machine 10 into the machine control, the operator may instruct the machine control to acquire an operating temperature reading from the sensor 110 at the location of the "effective" temperature of the machine 10. Alternatively, the machine control may automatically acquire the operating temperature at the some time either before or during the machining operation. For example, the NC program may include an instruction for the machine control to acquire automatically the operating temperature as the NC program is loaded into the machine control or executed. Once the operating temperature is obtained by the machine control, the machine control will select the proper compensation table 200, 300, 400, 500 as described above.

According to an alternative embodiment of the present invention, the compensation table 200 does not include a third column 206. Rather, thermal offset values are calculated dynamically as the machine control receives instructions from the NC program That is, first and second columns 202, 204, respectively, are populated with values 203, 205, respectively, as described above. However, thermal offset values are calculated as position commands are received by the machine control. According to the method of the present embodiment, each time the machine control receives a commanded position instruction from the NC program, the machine control obtains a value for the mechanical offset corresponding to the position instruction, acquires an "effective" machine temperature reading and calculates a thermal offset value using Equation (1). The offset values are then added to the commanded position value as described above to compensate for both mechanical and thermal positioning errors.

Figure 5:
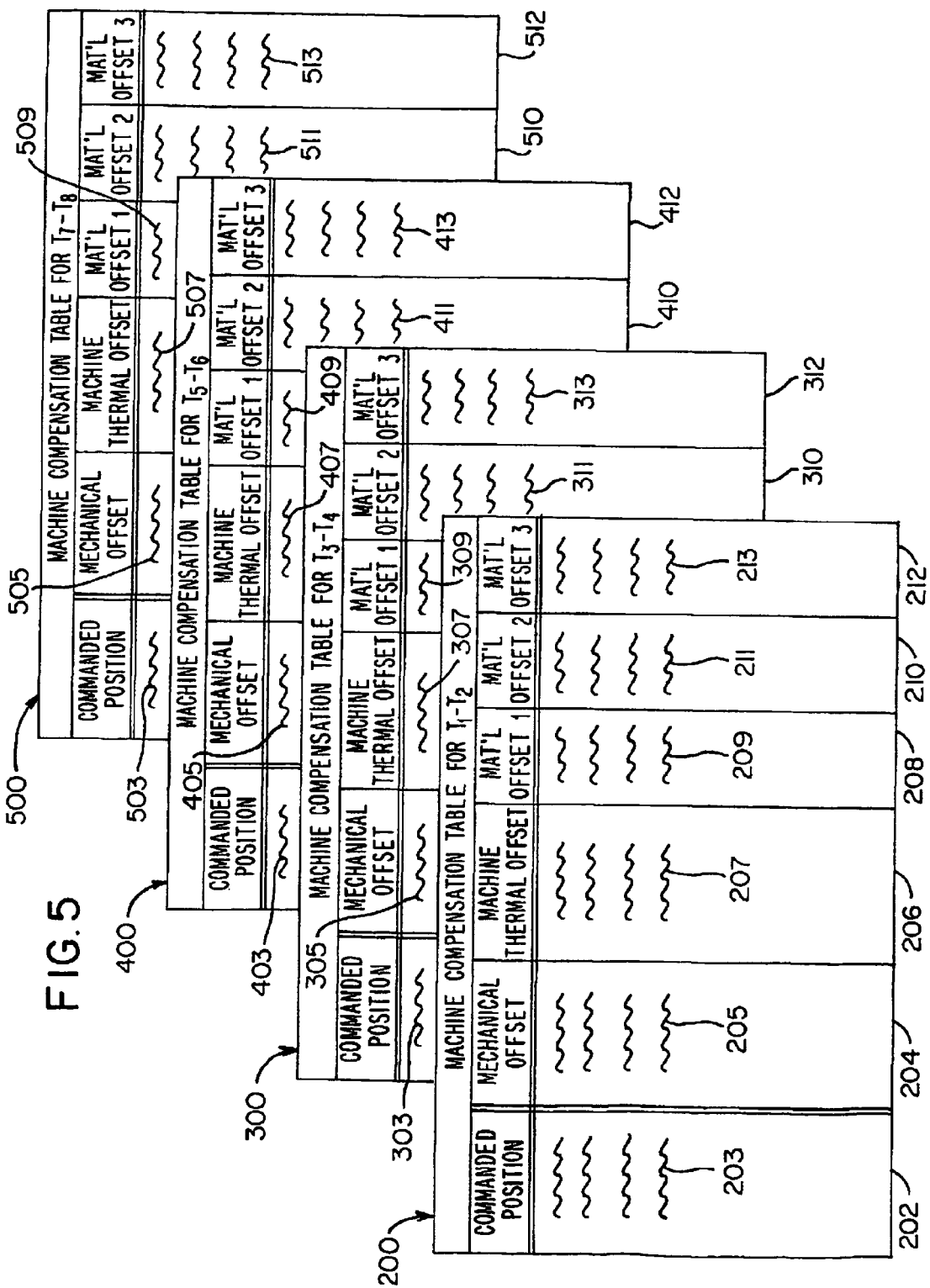

According to another aspect of the present invention, the method hereof may be used to calibrate the machine tool 10 for positioning errors due to machining a workpiece having a coefficient of thermal expansion which is different than the "effective" thermal coefficient $\alpha$ of the machine 10. With reference to FIG. 5, the compensation table 200 includes a fourth column 208 of workpiece thermal offset values 209, one such workpiece thermal offset value 209 corresponding to one of each of the commanded position values 203 of the first column 202. The fourth column 208 represents values calculated using Equation (1) to compensate for thermal positioning errors of the machine 10 due to thermal expansion of the workpiece "W" relative to the machine 10. For the purpose of using Equation (1) to calculate such workpiece thermal offset values 209 (which are represented in Equation (1) by the term $\Delta L$), any accepted value for the coefficient of thermal expansion of the material used to construct the workpiece may be used, or an "effective" thermal coefficient thereof may be calculated. The term $\Delta T$ represents the difference between the workpiece operating temperature (which is represented in Equation (1) by the term $T_f$) and a reference temperature of 68° F. (20° C.).

The compensation table 200 may be modified to permit selection of various workpiece materials. Fifth and sixth columns 210, 212, respectively, may be provided, each representing material thermal offset values 211, 213 calculated using Equation (1) based on unique workpiece materials. For example, the fourth column 208 may represent workpiece thermal offset values 209 calculated with Equation (1) based upon the coefficient of thermal expansion of aluminum, the fifth column 210 may represent workpiece thermal offset values 211 calculated with Equation (1) based upon the coefficient of thermal expansion of titanium and the sixth column 212 may represent workpiece thermal offset values 213 calculated with Equation (1) based upon the coefficient of thermal expansion of steel. Of course, more or less than the number of columns described herein may be provided without departing from either the spirit or the scope of the present invention.

Prior to the machining operation, the machine operator may enter manually into the machine control the material used to construct the workpiece to be machined. Based upon the operator's input, the machine control will access either the fourth, fifth or sixth column 208, 210, 212, respectively, and read the workpiece thermal offset values 209, 211, 213, respectively, thereof, together with the mechanical offset values 205 of the second column 204 and the machine thermal offset values 207 of the third column 206, to calculate a total offset value to compensate for all mechanical, machine thermal and workpiece thermal positioning errors. Alternatively, the NC program may include an instruction to the machine control concerning which column, as between columns 208, 210, 212, for reading workpiece thermal offset values.

As with the method described above with reference to FIG. 4, calculation of the workpiece thermal offset values 209, 211, 213 using Equation (1) requires the temperature of the workpiece to be known or approximated. The workpiece temperature may be manually entered into the machine control by the machine operator or it may be acquired automatically by the machine control, which may read data from a temperature sensor positioned on or near the workpiece at any suitable location therefor. As described above, where the machine control acquires the workpiece temperature reading automatically, such may be in response to an instruction by the operator or in response to an instruction provided in the NC program. Additional compensation tables 300, 400, 500 may be provided for temperature ranges $T_3-T_4$, $T_8-T_6$ and $T_7-T_8$, respectively, where compensation table 200 is provided for temperature range $T-T_2$ as described above. However, each compensation table 300, 400, 500 may include fourth, fifth and sixth columns representing thermal offset values for specific material selections, such as aluminum, titanium and steel, wherein the compensation table is selected in response to temperature input and the respective workpiece thermal offset column thereof is selected in response to workpiece material selection. In this manner, the machine tool 10 may be calibrated to compensate for mechanical, machine thermal and workpiece thermal positioning errors without modifying the NC program.

Where a member being tested according to the method hereof is not constrained whatsoever, the method hereof may be used to determine the "effective" thermal coefficient of the member. Accordingly, the present invention provides a method for determining the "effective" value of the thermal coefficient of a machine member. Moreover, the present invention provides a method for determining the "effective" value of the thermal coefficient of a machine member, with reference to the environmental conditions surrounding it.

As described above, the present invention provides a method for determining an "effective" value of the thermal coefficient of a machine comprised of members constructed of materials having differing individual thermal coefficient values. Moreover, the present invention provides a method for determining the "effective" value of the thermal coefficient of a machine comprised of members which are constrained from freely moving in response to changes in the temperatures thereof.

Furthermore, as described above, the present invention provides a method for determining an "effective" temperature of a machine, which such "effective" temperature" thereof may be used, for example, in performing thermal expansion calculations.

Moreover, as described above, the present invention provides a method for calibrating a machine wherein the true thermal characteristics of the machine are closely approximated, such as, with reference to an "effective" value of the thermal coefficient thereof The present invention furthermore provides a method for calibrating a machine wherein the thermal characteristics of a workpiece to be machined thereby are incorporated therein, and also provides a method for calibrating a machine wherein the thermal characteristics of a workpiece to be machined thereby are incorporated thereinto, and wherein a plurality of workpiece materials may be considered.

While the invention has been illustrated with reference to one or more preferred embodiments hereof, and such preferred embodiments have been described in considerable detail with reference to the drawings, it is not the intention of applicants that the invention be restricted to such detail. Rather, it is the intention of the applicants that the invention be defined by all equivalents of the preferred embodiments falling within the scope hereof.

We claim:

1. A method for calibrating a machine to compensate for thermal expansion/contraction thereof, characterized in that said method comprises the steps of:

determining an effective thermal coefficient of said machine;

generating a machine thermal compensation value for at least one of a predetermined number of reselected position values, said machine thermal compensation value being based on said effective thermal coefficient of said machine;

selecting a thermal coefficient of a workpiece to be machined by the machine;

generating a workpiece thermal compensation value based upon said thermal coefficient of said workpiece; and, adding said workpiece thermal compensation value to said machine thermal compensation value to obtain a total thermal offset compensation value to calibrate the machine.

2. The method of claim 1, further characterized in that said step of selecting a thermal coefficient of a workpiece includes the step of selecting a material to be machined, said material having said thermal coefficient associated therewith.

3. The method of claim 1, further characterized in that said thermal coefficient of said workpiece is selected in response to an instruction from an NC program.

4. A method for calibrating a machine to compensate for thermal expansion/contraction thereof, characterized in that said method comprises the steps of:

(a) determining an effective thermal coefficient of said machine;

(b) generating a machine thermal compensation value for at least one of a predetermined number of preselected position values to calibrate the machine, said machine thermal compensation value being based on said effective thermal coefficient of said machine;

further characterized in that said step of determining an effective thermal coefficient of said machine further comprises the steps of:

(c) selecting at least one predetermined location on said machine to monitor temperature during a test period;

(d) monitoring a distance between a first portion of said machine and a second portion of said machine;

(e) acquiring a temperature reading at said at least one predetermined location;

(f) recording aid distance and said temperature reading when said temperature reading is acquired and associating said distance with said temperature reading;

(g) repeating said steps (d)–(t) until said test period has expired;

(h) determining whether a sufficiently linear relationship exists between said distances and said temperature readings recorded in step (f);

(i) repeating aid steps (c)–(h) until said sufficiently linear relationship exists; and, (j) selecting said effective thermal coefficient based upon said linear relationship.

5. The method of claim 4, further characterized in that said at least one predetermined location includes one predetermined location.

6. The method of claim 4, further characterized in that said distances are collinear.

7. The method of claim 4, further characterized in that said test period is at least 24 hours.

8. The method of claim 4, further characterized in that said first portion of said machine has a first thermal coefficient, said second portion of said machine has a second thermal coefficient and said first thermal coefficient is different from said second thermal coefficient.

9. The method of claim 4, further characterized in that said temperature readings are acquired at a predetermined frequency.

10. The method of claim 9, further characterized in that said predetermined frequency has a period of 10 minutes.

11. The method of claim 4, further characterized in that said first portion of said machine is moveable relative to said second portion of said machine.

12. The method of claim 11, further characterized in that said first portion of said machine is constrained from moving freely relative to said second portion of said machine.

13. The method of claim 4, further characterized in that said step of determining whether a sufficiently linear relationship exists comprises the step of performing a statistical analysis on said recorded distances and said recorded temperature readings.

14. The method of claim 13, further characterized in that said step of performing a statistical analysis comprises the steps of determining a correlation coefficient; and, comparing said correlation coefficient with a coefficient reference.

15. The method of claim 14, further characterized in that said step of determining a correlation coefficient comprises the step of determining a Pearson Product Moment Correlation Coefficient.

* * * * *

UNITED STATES PATENT AND TRADEMARK OFFICE
CERTIFICATE OF CORRECTION

PATENT NO.    : 6,941,669 B2
DATED         : September 13, 2005
INVENTOR(S)   : Shivaswamy et al.

It is certified that error appears in the above-identified patent and that said Letters Patent is hereby corrected as shown below:

Column 1,
Line 5, after "filed" delete "Jan" and insert -- Jun --.

Column 2,
Line 2, after "thermal coefficents" delete "a" and insert -- $\propto$ --.
Line 25, after "structure" insert -- . --.

Column 6,
Line 40, after "supports 62," insert -- 64 --.

Column 7,
Line 39, after "thermal expansion" delete "a" and insert -- $\propto$ --.
Line 42, after "scope hereof" insert -- . --.

Column 8,
Line 9, after "hot spot" insert -- . --.

Column 10,
Line 15, after "R" insert -- = --.
Line 39, after "having" delete "an "value"" and insert -- an "$R^2$" value --.
Line 60, after "to the" delete "$X^2$" and insert -- $X_2$ --.

Column 11,
Line 5, after "from the" insert -- " --.
Line 34, after "thereof" insert -- . --.

Column 12,
Line 32, after "compensation table" insert -- 200, --.
Line 58, after "temperature at" delete "the".

Column 13,
Line 3, after "NC program" insert -- . --.
Line 38, after "term" delete "$T_f)$" and insert -- $T_f$) --.

Column 14,
Line 18, after "$T_3 - T_4$," delete "$T_B$" and insert -- $T_5$ --.
Line 19, after "temperature range" delete "T" and insert -- $T_1$ --.
Line 58, after "thereof" insert -- . --.

UNITED STATES PATENT AND TRADEMARK OFFICE
CERTIFICATE OF CORRECTION

PATENT NO. : 6,941,669 B2
DATED : September 13, 2005
INVENTOR(S) : Shivaswamy et al.

It is certified that error appears in the above-identified patent and that said Letters Patent is hereby corrected as shown below:

<u>Column 15,</u>
Line 3, after "intention of" insert -- the --.
Line 14, after "number of" delete "reselected" and insert -- preselected --.

<u>Column 16,</u>
Line 1, after "(f) recording" delete "aid" and insert -- said --.
Line 4, after "steps (d)-" delete "(t)" and insert -- (f) --.
Line 10, after "(i) repeating" delete "aid" and insert -- said --.

Signed and Sealed this

Twenty-eighth Day of March, 2006

JON W. DUDAS
*Director of the United States Patent and Trademark Office*